United States Patent
Onishi et al.

(10) Patent No.: US 9,468,419 B2
(45) Date of Patent: Oct. 18, 2016

(54) ULTRASONIC TRANSDUCER ELEMENT UNIT, PROBE, PROBE HEAD, ELECTRONIC DEVICE, AND ULTRASONIC DIAGNOSTIC DEVICE

(71) Applicant: SEIKO EPSON CORPORATION, Tokyo (JP)

(72) Inventors: Yasunori Onishi, Nagano (JP); Kanechika Kiyose, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 121 days.

(21) Appl. No.: 13/915,963

(22) Filed: Jun. 12, 2013

(65) Prior Publication Data

US 2013/0338507 A1    Dec. 19, 2013

(30) Foreign Application Priority Data

Jun. 13, 2012  (JP) .................................. 2012-133670

(51) Int. Cl.
*A61B 8/00* (2006.01)
*B06B 1/06* (2006.01)

(52) U.S. Cl.
CPC ........... *A61B 8/4494* (2013.01); *A61B 8/4444* (2013.01); *A61B 8/461* (2013.01); *A61B 8/462* (2013.01); *B06B 1/0622* (2013.01)

(58) Field of Classification Search
None
See application file for complete search history.

(56) References Cited

U.S. PATENT DOCUMENTS

| | | | |
|---|---|---|---|
| 6,515,402 B2 | 2/2003 | Klee et al. | |
| 7,259,032 B2 * | 8/2007 | Murata et al. | ............. 438/26 |
| 7,730,785 B2 | 6/2010 | Wado et al. | |
| 8,125,321 B2 | 2/2012 | Kojima et al. | |
| 2007/0016052 A1 * | 1/2007 | Fukukita | ............. G01S 15/8925 600/459 |
| 2010/0296692 A1 * | 11/2010 | Reiche | ......................... 381/423 |
| 2010/0305448 A1 * | 12/2010 | Dagonneau et al. | ......... 600/459 |
| 2012/0247217 A1 * | 10/2012 | Suzuki | ............................ 73/717 |

FOREIGN PATENT DOCUMENTS

| | | | | |
|---|---|---|---|---|
| JP | 50-028666 U | | 4/1975 | |
| JP | 2003-524907 A | | 8/2003 | |
| JP | 2005-051689 | * | 2/2005 | ............. H04R 1/28 |
| JP | 2005-051689 A | | 2/2005 | |
| JP | 2005-051690 A | | 2/2005 | |
| JP | 4043790 B2 | | 2/2008 | |
| JP | 2008-096113 A | | 4/2008 | |
| JP | 4254411 B2 | | 4/2009 | |
| JP | 2009-201053 A | | 9/2009 | |
| JP | 2010-147658 A | | 7/2010 | |
| JP | 2010-164331 A | | 7/2010 | |
| JP | 4640249 B2 | | 3/2011 | |
| JP | 2011-259274 A | | 12/2011 | |
| WO | 99/56500 A1 | | 11/1999 | |

* cited by examiner

*Primary Examiner* — Long V Le
*Assistant Examiner* — Marjan Saboktakin
(74) *Attorney, Agent, or Firm* — Global IP Counselors, LLP

(57) ABSTRACT

An ultrasonic transducer element unit includes a substrate, a first ultrasonic transducer element, and a projecting portion. The substrate includes openings being arranged in an array pattern and a main surface. The first ultrasonic transducer element is configured at a first opening of the openings on the main surface of the substrate and has a first height in a vertical direction from the main surface. The projecting portion is configured not to overlap with the first ultrasonic transducer element in a planar view in a thickness direction of the substrate on the main surface and having a second height which is greater than the first height in the vertical direction.

10 Claims, 12 Drawing Sheets

ULTRASONIC TRANSDUCER ELEMENT UNIT, PROBE, PROBE HEAD, ELECTRONIC DEVICE, AND ULTRASONIC DIAGNOSTIC DEVICE

CROSS-REFERENCE TO RELATED APPLICATIONS

This application claims priority to Japanese Patent Application No. 2012-133670 filed on Jun. 13, 2012. The entire disclosure of Japanese Patent Application No. 2012-133670 is hereby incorporated herein by reference.

BACKGROUND

1. Technical Field

The present invention relates to an ultrasonic transducer element unit, a probe and a probe head that use the ultrasonic transducer element unit, and an electronic device and an ultrasonic diagnostic device that use the probe.

2. Related Art

As described in Japanese Laid-Open Patent Publication No. 20110-147658, for example, an ultrasonic transducer element chip is provided with a substrate. Openings are formed on the substrate in an array pattern. An ultrasonic transducer element chip is provided in each opening. The ultrasonic transducer element has a vibrating membrane. The vibrating membrane covers an opening from a surface of the substrate. An ultrasonic wave is generated in each ultrasonic transducer element in response to the vibration of the vibrating membrane.

SUMMARY

A piezoelement is formed on the surface of the vibrating membrane in the excitation of the vibration. The piezoelement is projected from the surface of the substrate. Accordingly, when pressing a probe of an ultrasonic diagnostic device against a target (here, it is human body), the piezoelement receives the reaction force from the target. The reactive force of the target affects to the vibrating membrane directly, so that there was a case that the vibrating membrane, that is, the ultrasonic transducer element was damaged.

At least one aspect of the present invention, an ultrasonic transducer element unit that reduces a risk for damage to an ultrasonic transducer element is provided. The ultrasonic transducer element unit includes a substrate, a first ultrasonic transducer element, and a projecting portion. The substrate includes openings being arranged in an array pattern and a main surface. The first ultrasonic transducer element is configured at a first opening of the openings on the main surface of the substrate and has a first height in a vertical direction from the main surface. The projecting portion is configured not to overlap with the first ultrasonic transducer element in a planar view in a thickness direction of the substrate on the main surface and having a second height which is greater than the first height in the vertical direction.

BRIEF DESCRIPTION OF THE DRAWINGS

Referring now to the attached drawings which form a part of this original disclosure.

DETAILED DESCRIPTION OF EXEMPLARY EMBODIMENTS

Hereinafter, embodiments of the invention will be explained with reference to the attached drawings. By the way, the embodiments explained below shall not be construed as unreasonably limiting the subject matter of the invention described in the claims, and all the elements explained in the embodiments are not necessarily essential to the solving means of the present invention.

(1) Overall Configuration of the Ultrasonic Diagnostic Device

Figure 1:
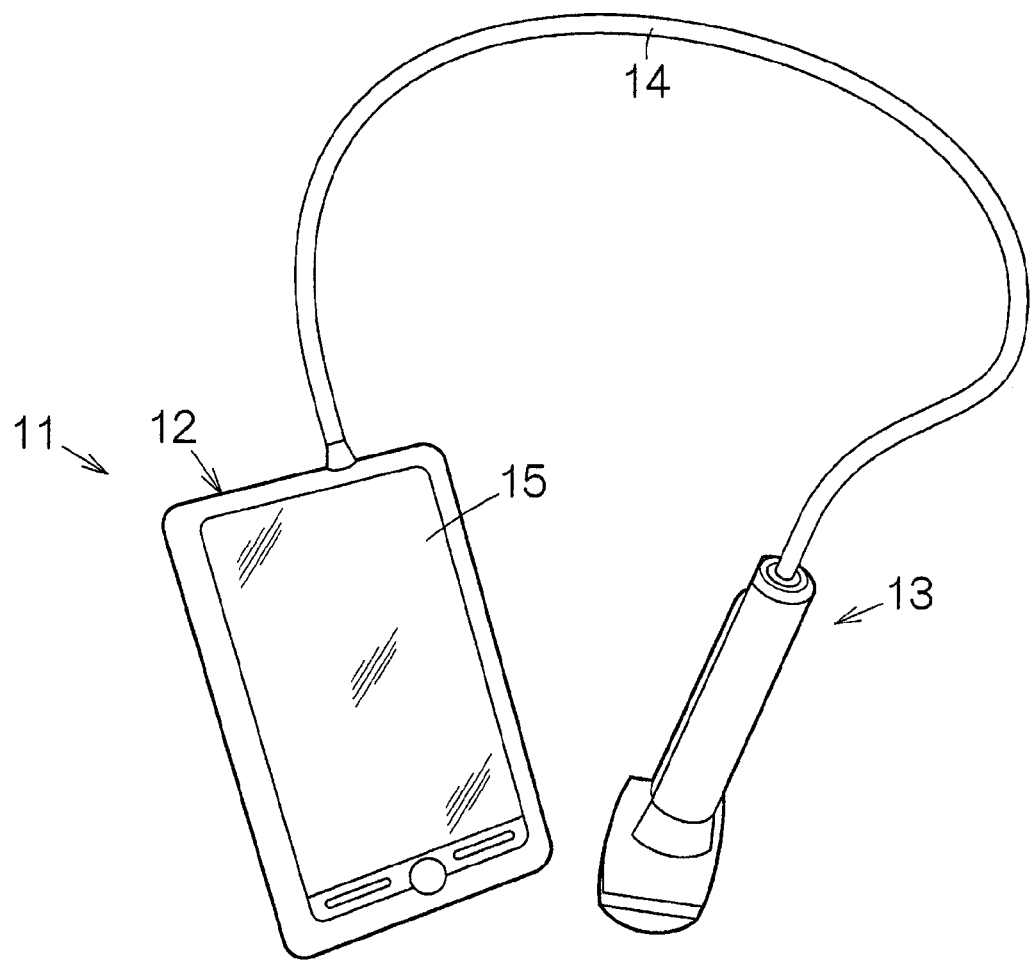
FIG. 1 is a perspective view schematically showing a concrete example of an electronic device, that is, an ultrasonic diagnostic device according to one embodiment of the present invention.

FIG. 1 schematically shows a configuration of an ultrasonic diagnostic device 11, that is, a concrete example of an electronic device according to an embodiment of the present invention. The ultrasonic diagnostic device 11 is provided with a device terminal 12 and an ultrasonic probe (probe) 13. The device terminal 12 and the ultrasonic probe 13 are connected to each other through a cable 14. The device terminal 12 and the ultrasonic probe 13 communicate an electric signal through the cable 14. A display panel (display device) 15 is incorporated in the device terminal 12. A screen of the display panel 15 is exposed on a surface of the device terminal 12. As described later, in the device terminal 12, an image is generated based on ultrasonic waves detected with the ultrasonic probe 13. Imaged detection results are displayed on the screen of the display panel 15.

Figure 2:
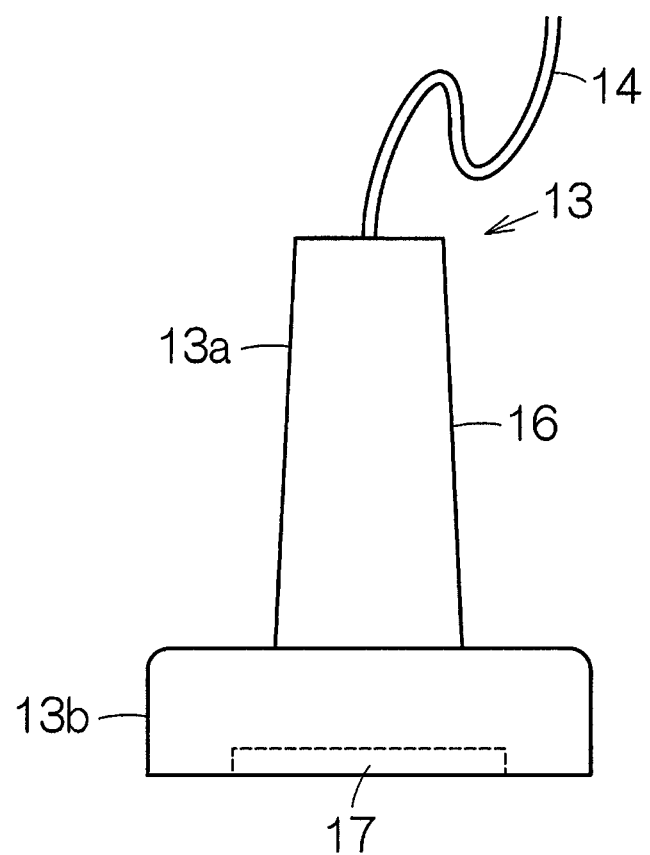
FIG. 2 is an enlarged front view of an ultrasonic probe.

As shown in FIG. 2, the ultrasonic probe 13 has a case 16. An ultrasonic transducer element unit (hereinafter referred to as "element unit") 17 is accommodated in the case 16. A surface of the element unit 17 can be exposed on a surface of the case 16. The element unit 17 outputs ultrasonic waves from the surface thereof, and receives reflected waves of ultrasonic waves. Also, the ultrasonic probe 13 can be provided with a probe head 13b removably coupled with a probe main body 13a. In such an instance, the element unit 17 can be incorporated in the case 16 of the probe head 13b.

Figure 3:
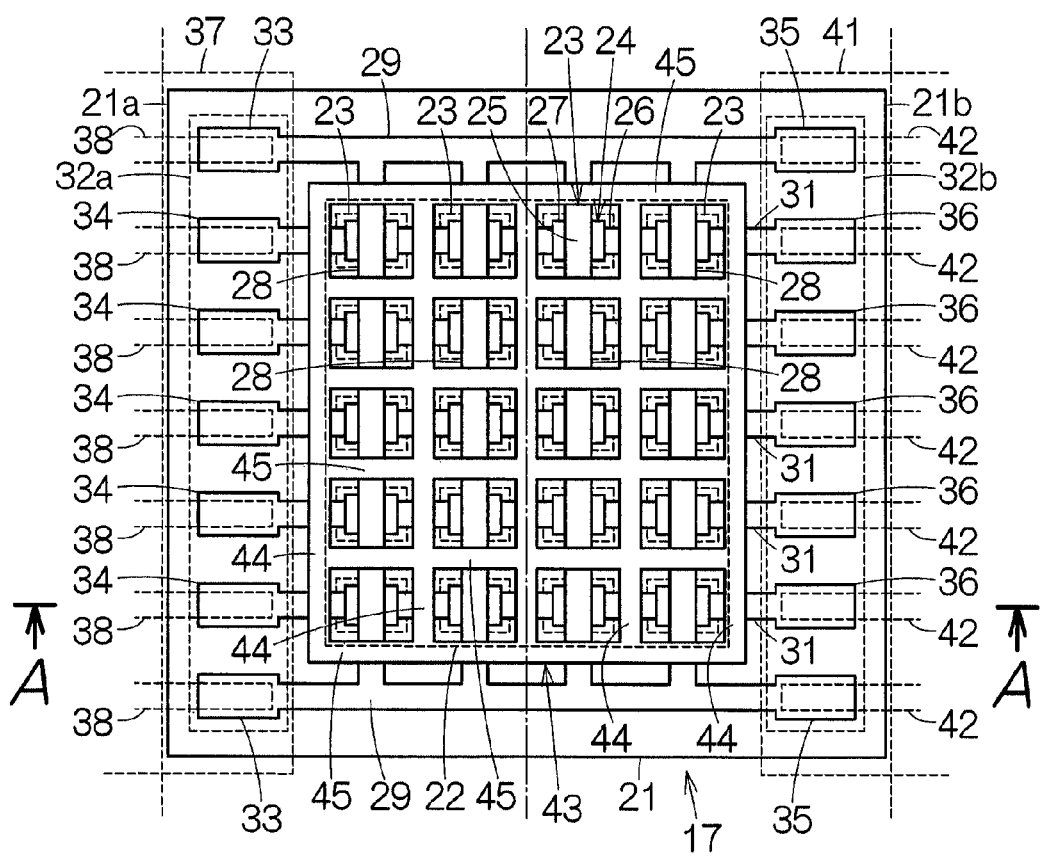
FIG. 3 is an enlarged plan view of an ultrasonic transducer element unit according to the first embodiment.

FIG. 3 schematically shows a plan view of the ultrasonic transducer element unit 17 according to the first embodiment. The element unit 17 is provided with a base body 21. An element array 22 is formed on the base body 21. The element array 22 is constructed with an arrangement of ultrasonic transducer elements (hereinafter referred to as "elements") 23. The arrangement is formed in a matrix having a plurality of rows and a plurality of columns. Each element 23 has a piezoelectric element section 24. The piezoelectric element section 24 is configured with an upper electrode 25, a lower electrode 26, and a piezoelectric film 27. The piezoelectric film 27 is placed between the upper electrode 25 and the lower electrode 26 in each element 23. The element unit 17 is configured as one ultrasonic transducer element chip.

A plurality of first electric conductors 28 is formed on a surface of the base body 21. The first electric conductors 28 extend in a row direction of the arrangement in parallel to each other. One first electric conductor 28 is assigned to each row of the elements 23. One first electric conductor 28 is provided in common with respect to the piezoelectric films 27 of the elements 23 aligned in the row direction of the arrangement. The first electric conductors 28 form the upper electrode 25 in each element 23, respectively. Both ends of the first electric conductors 28 are connected to a pair of extraction wirings 29, respectively. The extraction wirings 29 extend in a column direction of the arrangement in parallel to each other. Therefore, all the first electric conductors 28 have the same length. In this manner, the upper electrode 25 is provided in common with respect to the elements 23 of the entire matrix.

A plurality of second electric conductors 31 is formed on the surface of the base body 21. The second electric conductors 31 extend in a column direction of the arrangement in parallel to each other. One second electric conductor 31 is assigned to each column of the elements 23. One second electric conductor 31 is provided in common with respect to the piezoelectric films 27 of the elements 23 aligned in the column direction of the arrangement. Power distribution to the elements 23 is switched for each column. Line scanning or sector scanning is achieved corresponding to such switching of power distribution. Since the elements 23 in one column output ultrasonic waves at the same time, the number of the elements 23 in one column, that is, the number of rows of the arrangement can be determined based on the output level of ultrasonic waves. For example, the number of rows can be set to be around 10-15. In the drawing, four rows are illustrated for simplicity. The number of columns of the arrangement can be determined based on the extent of an area to be scanned. For example, the number of columns can be set to be 128 or 256. In the drawing, five columns are illustrated for simplicity. Also, regarding the arrangement, a zigzag pattern can be used. In the zigzag pattern, a group of the elements 23 in an even column can be displaced with respect to a group of the elements 23 in an odd column by one-half of the row pitch. The number of the elements in one of an odd column and an even column can be smaller than the number of the elements in the other of an odd column and an even column by one. Furthermore, the roles of the upper electrode 25 and the lower electrode 26 can be switched. Specifically, the lower electrode can be connected in common to the elements 23 of the entire matrix, and the upper electrode can be connected in common to the elements 23 in each column of the arrangement.

The outline of the base body 21 has a first side 21a and a second side 21b that are opposed and partitioned by a pair of straight lines parallel to each other. A first terminal array 32a of one line is arranged between the first side 21a and the outline of the element array 22. A second terminal array 32b of one line is arranged between the second side 21b and the outline of the element array 22. One line of the first terminal array 32a can be formed parallel to the first side 21a. One line of the second terminal array 32b can be formed parallel to the second side 21b. The first terminal array 32a is configured with a pair of upper electrode terminals 33 and a plurality of lower electrode terminals 34. In the same manner, the second terminal array 32b is configured with a pair of upper electrode terminals 35 and a plurality of lower electrode terminals 36. The upper electrode terminals 33, 35 are connected to both ends of each of the extraction wiring 29, respectively. It is sufficient for the extraction wirings 29 and the upper electrode terminals 33, 35 to be formed plane-symmetrically with respect to a vertical plane that bisects the element array 22. The lower electrode terminals 34, 36 are connected to both ends of each of the second electric conductors 31, respectively. It is sufficient for the second electric conductors 31, the lower electrode terminals 34, 36 to be formed plane-symmetrically with respect to the vertical plane that bisects the element array 22. Here, the outline of the base body 21 is formed in a rectangle. The outline of the base body 21 can also be square or trapezoidal.

A first flexible wiring board (hereinafter referred to as "first wiring board") 37 is coupled with the base body 21. The first wiring board 37 covers the first terminal array 32a. Conductive lines, that is, first signal lines 38 are formed at one end of the first wiring board 37 corresponding to the upper electrode terminals 33 and the lower electrode terminals 34, respectively. The first signal lines 38 are respectively opposed to the upper electrode terminals 33 and the lower electrode terminals 34, and respectively bonded thereto. Similarly, a second flexible wiring board (hereinafter referred to as "second wiring board") 41 covers the base body 21. The second wiring board 41 covers the second terminal array 32b. Conductive lines, that is, second signal lines 42 are formed at one end of the second wiring board 41 corresponding to the upper electrode terminals 35 and the lower electrode terminals 36, respectively. The second signal lines 42 are respectively opposed to the upper electrode terminals 35 and the lower electrode terminals 36, and respectively bonded thereto.

A grid element 43 is fixed on the surface of the base body 21. The grid element 43 is provided with a plurality of first long pieces 44 that extend in a row direction of the element array 22, and a plurality of second long pieces 45 that extend in a column direction of the element array 22. The first long pieces 44 are reciprocally arranged in parallel. The second long pieces 45 are reciprocally arranged in parallel. The first long pieces 44 and the second long pieces 45 are arranged in a position shifted from the elements 23 in a direction parallel to the surface of the base body 21. The single-row element 23 is placed between the first long pieces 44 that are adjacent to each other. The single-row element 23 is placed between the second long pieces 45 that are adjacent to each other. Thus, the overlap of the elements 23 and the grid element 43 is avoided.

Figure 4:
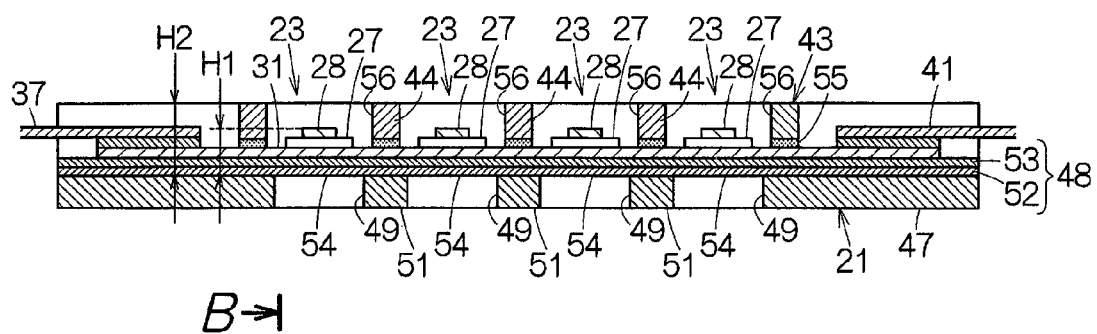
FIG. 4 is a cross-section view along the A-A line of FIG. 3.

As shown in FIG. 4, the base body 21 is provided with a substrate 47 and a flexible film 48. The flexible film 48 is formed on the surface of the substrate 47 entirely. The openings 49 are formed in each of elements 23 in the substrate 47, respectively. The openings 49 are arranged in an array pattern to the substrate 47. Partition walls 51 are laid out between the openings 49 that are adjacent to each other. Each of the openings 49 is separated by the partition wall 51. The thickness of the partition walls 51 corresponds to an interval of a space between the openings 49. The partition wall 51 defines two wall surfaces in planes extending in parallel to each other. The wall thickness corresponds to the interval between the wall surfaces. Specifically, the wall thickness can be defined by the length of a vertical line that is orthogonal to the wall surfaces and is wedged between the wall surfaces.

The flexible film 48 is constructed of a silicon oxide ($SiO_2$) layer 52 layered on the surface of the substrate 47, and a zirconium oxide ($ZrO_2$) layer 53 layered on a surface of the silicon oxide layer 52. The flexible film 48 contacts to the openings 49. In this manner, a part of the flexible film 48 serves as the vibrating membrane 54 corresponding to the outline of the opening 49. The film thickness of the silicon oxide layer 52 can be determined based on the resonance frequency.

The second electric conductor 31, the piezoelectric film 27, and the first electric conductor 28 are layered on a surface of the vibrating membrane 54 in this order. For the second electric conductor 31, a layered film of titanium (Ti), iridium (Ir), platinum (Pt), and titanium (Ti) can be used, for example. The piezoelectric film 27 can be formed of piezoelectric zirconate titanate (PZT), for example. The first electric conductor 28 can be formed of iridium (Ir), for example. Another conductive material can be used for the first electric conductor 28 and the second electric conductor 31, and another piezoelectric material can be used for the piezoelectric film 27. Here, the piezoelectric film 27 completely covers the second electric conductor 31 under the first electric conductor 28. The function of the piezoelectric film 27 prevents short circuits between the first electric conductor 28 and the second electric conductor 31.

Adhesive agent 55 is used to fix the grid element 43. The adhesive agent 55 is wedged between the grid element 43 and the base body 21. The first long pieces 44 and the second long pieces 45 are placed in a position that does not overlap with the openings 49 in a planar view from a thickness direction of the base body 21. Specifically, the grid element 43 contacts with the surface of the base body 21 in outside of the outline of the openings 49. The grid element 43 is connected to the partition walls between the elements 23. The grid element 43 has the second height H2 which is greater than the first height H1 of the elements 23. The first height H1 and the second height H2 are defined in a vertical direction from the surface (main surface) of the substrate 47. The grid element 43 is placed between the first long pieces 44 that are adjacent to each other, and a space of rectangular solid 56 is laid out between the second long pieces that are adjacent to each other. The elements 23 are contained in each of the spaces 56.

The protection film 57 is layered on the surface of the base body 21. The protection film 57 is filled at least in each of the spaces 56. The surface of the protection film 57 has the height H2 which is the same height H2 of the grid element 43. Thus, the protection film 57 covers the elements 23. Here, the protection film 57 entirely covers the surface of the base body 21. As a result, not only the element array 22, but also the first and second terminal arrays 32a, 32b, and the first and second wiring boards 37, 41 are covered by the protection film 57. For example, a silicon resin film can be used for the protection film 57. The protection film 57 protects a configuration of the element array 22, a junction of the first terminal array 32a and the first wiring board 37, and a junction of the second array 32b and the second wiring board 41.

Figure 5:
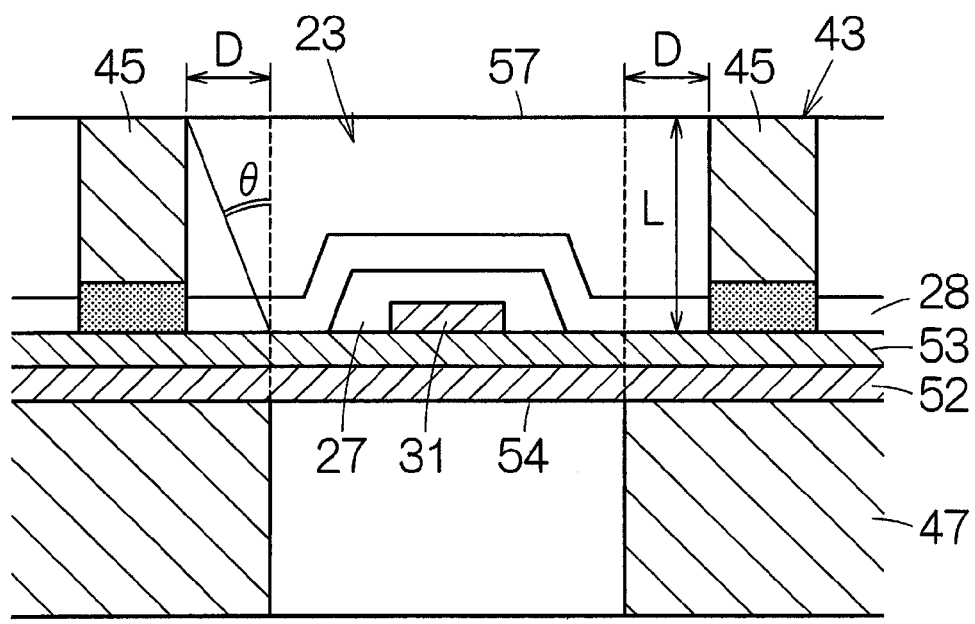
FIG. 5 is an enlarged cross-section view of an ultrasonic transducer element along the B-B line of FIG. 4.

As shown in FIG. 5, a distance D from the outline of the vibrating membrane 54 to the second long pieces 45 of the grid element 43 and a distance L from the surface of the vibrating membrane 54 to the top surface of the grid elements 43 are established as follows.

[Equation 1]

$$D = L \cdot \tan \theta \quad (1)$$

Here, an angle θ identifies an angle of inclination from a vertical surface defined by an edge of the vibrating membrane 54 that is the closest to the second long pieces 45 of the grid element 43. The angle θ corresponds to an angle of oscillation of the ultrasonic beam. For example, when an acoustic velocity of the protection film 57 is 800 m/s, and an acoustic velocity of biological object (target) that the protection film 57 contacts with is 1600 m/s, the angle θ can be set more than 16 degrees. The thickness of the protection film 57 can be set in one quarter of the wavelength of the ultrasonic frequency. As a result, the protection film 57 can be functioned as an acoustic matching layer. The distance D can be defined between the vertical surface defined by the edge of the vibrating membrane 54 that is closest to the second long pieces 45 of the grid element 43 and top edges of the second long pieces 45.

(2) Circuit Configuration of the Ultrasonic Diagnostic Device

Figure 6:
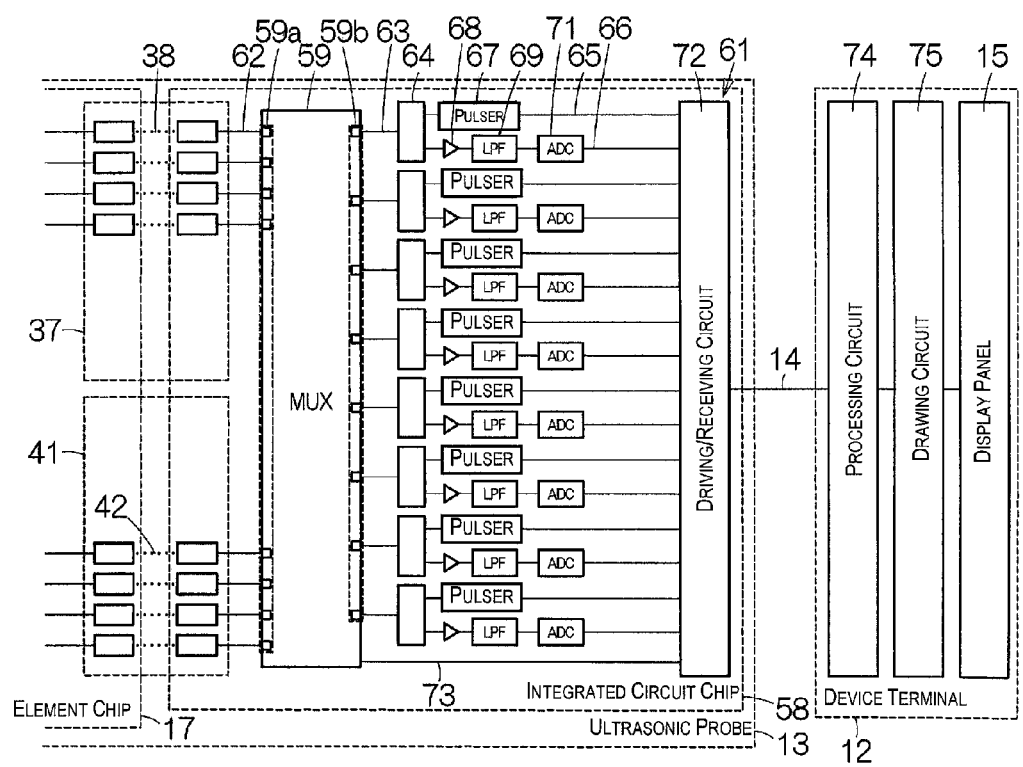
FIG. 6 is a block diagram schematically showing a circuit configuration of an ultrasonic diagnostic device.

As shown in FIG. 6, the ultrasonic diagnostic device 11 is provided with an integrated circuit chip 58 that is electrically connected to the element unit 17. The integrated circuit chip 58 provided with a multiplexer 59 and a transmitting and receiving circuit 61. The multiplexer 59 is provided with a group of ports 59a on the element unit 17 side and a group of ports 59b on the transmitting and receiving circuit 61 side. The first signal lines 38 and the second signal lines 42 are connected to the group of ports 59a on the element unit 17 side. In this manner, the group of ports 59a is connected to the element array 22. Here, a prescribed number of signal lines 63 within the integrated circuit chip 58 is connected to the group of ports 59b on the transmitting and receiving circuit 61 side. The prescribed number corresponding to the number of columns of the elements 23 output simultaneously when scanning. The multiplexer 59 controls an interconnection between the ports on the cable 14 side and the ports on the element unit 17 side.

The transmitting and receiving circuit 61 has a prescribed number of changing switches 64. The changing switches 64 are connected to the corresponding signal lines 63, respectively. The transmitting and receiving circuit 61 has a transmission channel 65 and a reception channel 66 for each of the changing switches 64. The transmission channel 65 and the reception channel 66 are connected to the changing switch 64 in parallel. The changing switch 64 selectively connects the transmission channel 65 and the reception channel 66 to the multiplexer 59. A pulsar 67 is incorporated in the transmission channel 65. The pulsar 67 outputs a pulse signal at a frequency corresponding to the resonance frequency of the vibrating membrane 54. An amplifier 68, a low-pass filter (LPF) 69, and an analog-digital converter (ADC) 71 are incorporated in the reception channel 66. A detection signal of each of the elements 23 is amplified, and converted into a digital signal.

The transmitting and receiving circuit 61 has a driving/receiving circuit 72. The transmission channel 65 and the reception channel 66 are connected to the driving/receiving circuit 72. The driving/receiving circuit 72 controls the pulsar 67 simultaneously depending on the state of scanning. The driving/receiving circuit 72 receives a digital signal of a detection signal depending on the state of scanning. The driving/receiving circuit 72 is connected to the multiplexer 59 through a control line 73. The multiplexer 59 conducts control of the interconnection based on a control signal supplied from the driving/receiving circuit 72.

A processing circuit 74 is incorporated in the device terminal 12. The processing circuit 74 can be provided with a central processing unit (CPU) and a memory, for example. The entire operation of the ultrasonic diagnostic device 11 is controlled in accordance with processing of the processing circuit 74. The processing circuit 74 controls the driving/receiving circuit 72 in accordance with instructions input by a user. The processing circuit 74 generates an image in accordance with a detection signal of the element 23. The image is specified by drawing data.

A drawing circuit 75 is incorporated in the device terminal 12. The drawing circuit 75 is connected to the processing circuit 74. The display panel 15 is connected to the drawing circuit 75. The drawing circuit 75 generates a driving signal in response to drawing data generated in the processing circuit 74. The driving signal is sent to the display panel 15. As a result, an image is displayed on the display panel 15.

(3) Operation of the Ultrasonic Diagnostic Device

Next, the operation of the ultrasonic diagnostic device 11 will be explained briefly. The processing circuit 74 gives the driving/receiving circuit 72 instructions to transmit and receive ultrasonic waves. The driving/receiving circuit 72 supplies a control signal to the multiplexer 59, and supplies a driving signal to each of the pulsars 67. The pulsar 67 outputs a pulse signal in response to the supply of the driving signal. The multiplexer 59 connects the port of the group of ports 59a to the port of the group of ports 59b in response to the instructions of the control signal. The pulse signal is supplied to the elements 23 for each column through the upper electrode terminals 33, 35 and the lower electrode terminals 34, 36 in response to the selection of the port. The vibrating membrane 54 vibrates in response to the supply of the pulse signal. As a result, desired ultrasonic waves are emitted toward a target (for example, the inside of a human body).

After ultrasonic waves are transmitted, the changing switch 64 is switched. The multiplexer 59 maintains the connection relation of the ports. The changing switch 64 establishes a connection between the reception channel 66 and the signal line 63 instead of a connection between the transmission channel 65 and the signal line 63. Reflected waves of ultrasonic waves vibrate the vibrating membrane 54. As a result, a detection signal is output from the element 23. The detection signal is converted into a digital signal, and sent into the driving/receiving circuit 72.

Transmission and reception of ultrasonic waves are repeated. For repeating transmission and reception of ultrasonic waves, the multiplexer 59 changes the connection relation of the ports. As a result, line scanning or sector scanning is realized. When scanning is completed, the processing circuit 74 generates an image based on the digital signal of the detection signal. The generated image is displayed on the screen of the display panel 15.

The top surface of the grid element 43 is defined in a position higher than the height H1 of the elements 23 in the element unit 17. Thus, when the surface of the base body 21 is pressed against the target, the grid element 43 can receive the reaction force from the target earlier than the elements 23. The grid element 43 supports the reaction force from the target. In this manner, the effect of external-force to the elements 23 can be prevented. The breakage of the elements 23 is reliably prevented. In addition, the protection film 57 is entirely formed on the top surface of the grid element 43 so that the effect of the reaction force from the target to the protection film 57 can be suppressed. The deformation of the protection film 57 can be prevented.

Figure 7:
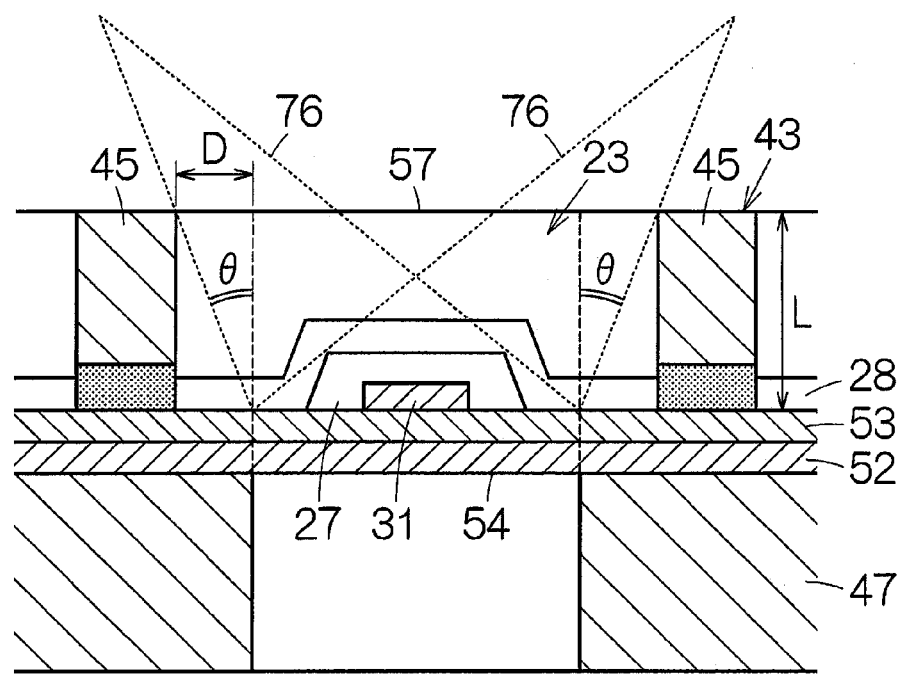
FIG. 7 corresponds to FIG. 5, and the drawing is an enlarged cross-section view of the ultrasonic transducer element schematically showing oscillation of ultrasonic beam.

As shown in FIG. 7, the elements 23 irradiate the ultrasonic beam 76 in the element unit 17. The elements 23 can scan the ultrasonic beam 76 around the rotation axis in parallel with the row direction of the element array 22. In a case that the ultrasonic beam 76 is inclined relative to the vertical direction of the surface of the vibrating membrane 54, as a distance increases from the surface of the vibrating membrane 54, the ultrasonic beam 76 increases a distance from the elements 23 in a direction parallel to the surface of the vibrating membrane 54. When a distance D is set in response to a maximum angle of inclination of the ultrasonic beam 76, the interference between the second long pieces 45 of the grid element 43 and the ultrasonic beam 76 can be prevented.

(4) Method for Manufacturing Ultrasonic Transducer Element Unit

Figure 8:
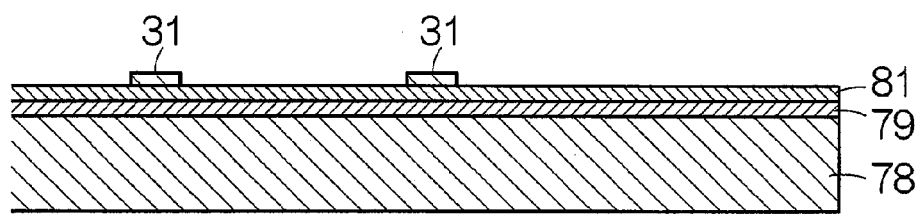
FIG. 8 is a partial enlarged vertical sectional view schematically showing a flexible film and the second electric conductor on a silicon wafer.

As shown in FIG. 8, the second electric conductor 31 and the lower electrode terminals 34, 36 (not shown in the drawings subsequent to FIG. 8) are formed on a surface of a silicon wafer 78 for each element unit 17. Prior to forming the second electric conductor 31 and the lower electrode terminals 34, 36, a silicon oxide film 79 and a zirconium oxide film 81 are formed on the surface of the silicon wafer 78 in sequence. A conductive film is formed on a surface of the zirconium oxide film 81. The conductive film is constructed as a layered film of titanium, iridium, platinum, and titanium. The second electric conductor 31 and the lower electrode terminals 34, 36 are formed from the conductive film by the photolithographic technique.

Figure 9:
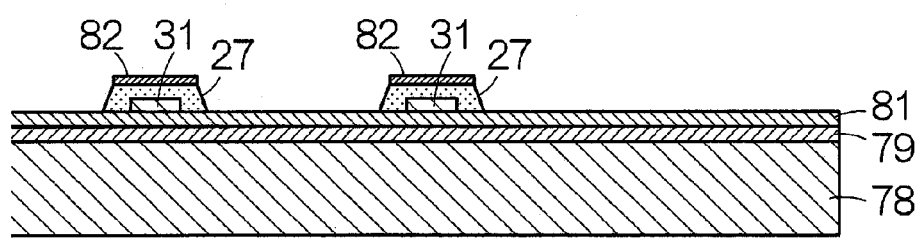
FIG. 9 is a partial enlarged vertical sectional view schematically showing a piezoelectric film and the first conductive film formed on the second electric conductor.

As shown in FIG. 9, the piezoelectric film 27 and the first conductive film 82 are formed on a surface of the second electric conductor 31 for each element 23. Prior to forming the piezoelectric film 27 and the first conductive film 82, a piezoelectric material film and a solid film of an electrical conducting material are formed on the surface of the silicon wafer 78. The piezoelectric material film is composed of a PZT film. The solid film of the electrical conducting material is composed of iridium film. The piezoelectric film 27 and the first conductor film 82 are formed from the piezoelectric material film and the solid film of the electrical conducting material for each element 23 by the photolithographic technique.

Figure 10:
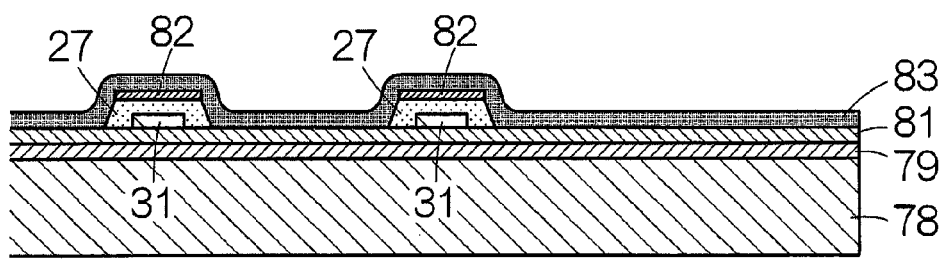
FIG. 10 is a partial enlarged vertical sectional view schematically showing a solid film of an electrical conducting material covering the silicon wafer.

Next, as shown in FIG. 10, the solid film 83 of the electrical conducting material is formed on the surface of the silicon wafer 78. The solid film 83 of the electrical conducting material covers each of the first conductive films 82. The first conductive films 82 connect the solid film 83 with respect to each other. And, the second conductive film is formed from the solid film 83 by a photolithographic technique. The second conductive film extends in a direction perpendicular to the second electric conductors 31 and intersects the second electric conductors 31 in sequence. The second conductive film connects the respective first conductive films 82 in the row direction of the element array 22.

The second conductive film forms the first electric conductors 28, the extraction wirings 29, and the upper electrode terminals 33, 35. A part of the second conductive film overlaps with the first conductive film 82 and the upper electrode 25 is formed with the first conductive films 82.

Figure 11:
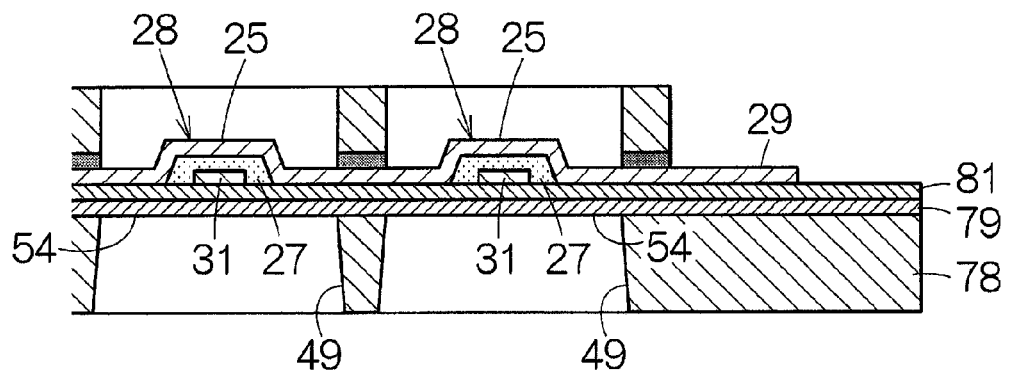
FIG. 11 is a partial enlarged vertical sectional view schematically showing openings and a grid element formed on the silicon wafer.

Next, as shown in FIG. 11, the openings 49 of an array pattern are formed from the reverse surface of the silicon wafer 78. For forming the openings 45, an etching treatment is conducted. The silicon oxide film 79 serves as an etching stop layer. The vibrating membrane 54 is divided into the silicon oxide film 79 and the zirconium oxide film 81. After the openings 49 are formed, the grid element 43 is adhered in each element unit 17 on the surface of the silicon wafer 78. The grid element 43 is superimposed on the surface of the silicon wafer 78. After adhering, each element unit 17 is cut out from the silicon wafer 78.

(5) Ultrasonic Transducer Element Unit According to Another Embodiment

Figure 12:
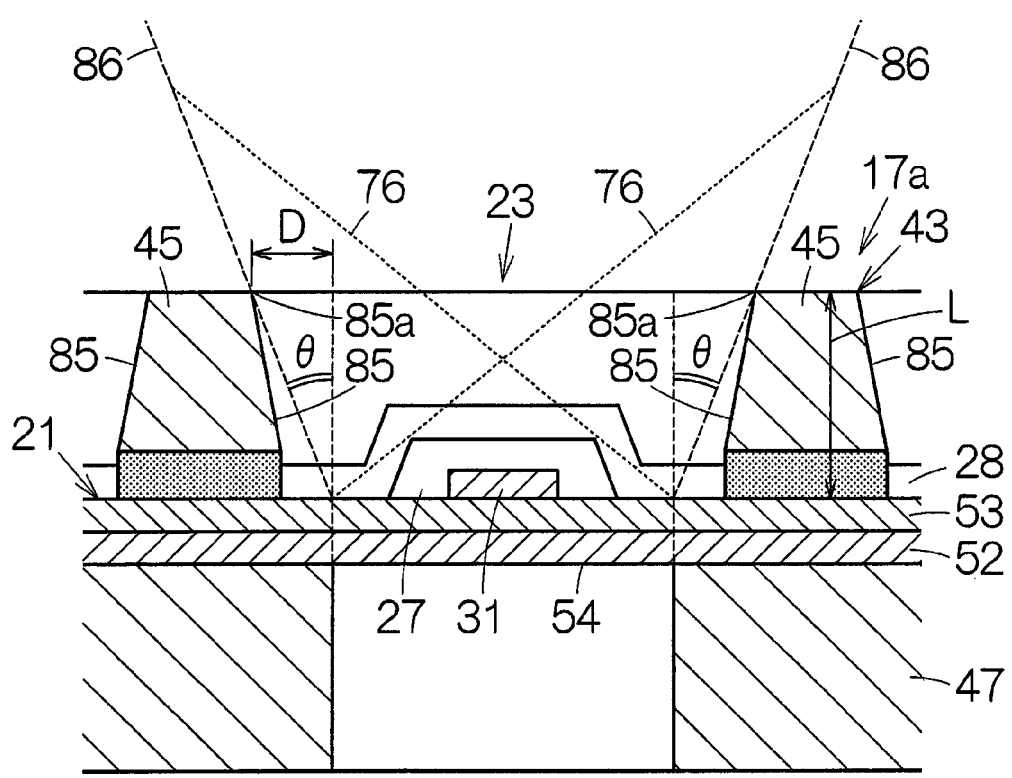
FIG. 12 corresponds to FIG. 5, and the drawing is a partial enlarged cross-section view of an ultrasonic transducer element unit according to the second embodiment.

FIG. 12 schematically shows a configuration of the ultrasonic transducer element unit 17a according to the second embodiment. In the second embodiment, the second long pieces 45 of the grid element 43 have a side surface (a side surface facing the element 23) of an inclined surface 85. The inclined surface 85 can be formed by a flat surface, for example. As a distance increases from the surface of the base body 21 in a vertical direction, the inclined surface 85 increases a distance from the element 23 in a planar view. In this point, an edge line 85a forming the top edge of the inclined surface 85, and an inclined angle (=angle θ) of a flat surface 86 connecting an edge of the vibrating membrane 54 that is closest to the second long pieces 45 can be defined by the same [Equation 1] as described above. Other configurations are the same as the previous description.

In the element unit 17a, the element 23 irradiates the ultrasonic beam 76. The element 23 can scan the ultrasonic beam 76 around the rotation axis in parallel with the row direction of the element array 22. In a case that the ultrasonic beam 76 inclines relative to the vertical direction of the surface of vibrating membrane 54, as a distance increases from the surface of the vibrating membrane 54, the ultrasonic beam 76 increases a distance from the element 23 in a direction parallel to the surface of the vibrating membrane 54. As described above, when a distance D is set in response to a maximum angle of inclination of the ultrasonic beam 76, the interference between the second long pieces 45 of the grid element 43 and the ultrasonic beam 76 can be prevented. Here, the thickness of wall of the second long pieces 45 can be increased compare to the grid element 43 according to the first embodiment. Therefore, the strength of the grid element 43 can be improved.

(6) Ultrasonic Transducer Element Unit According to Still Another Embodiment

Figure 13:
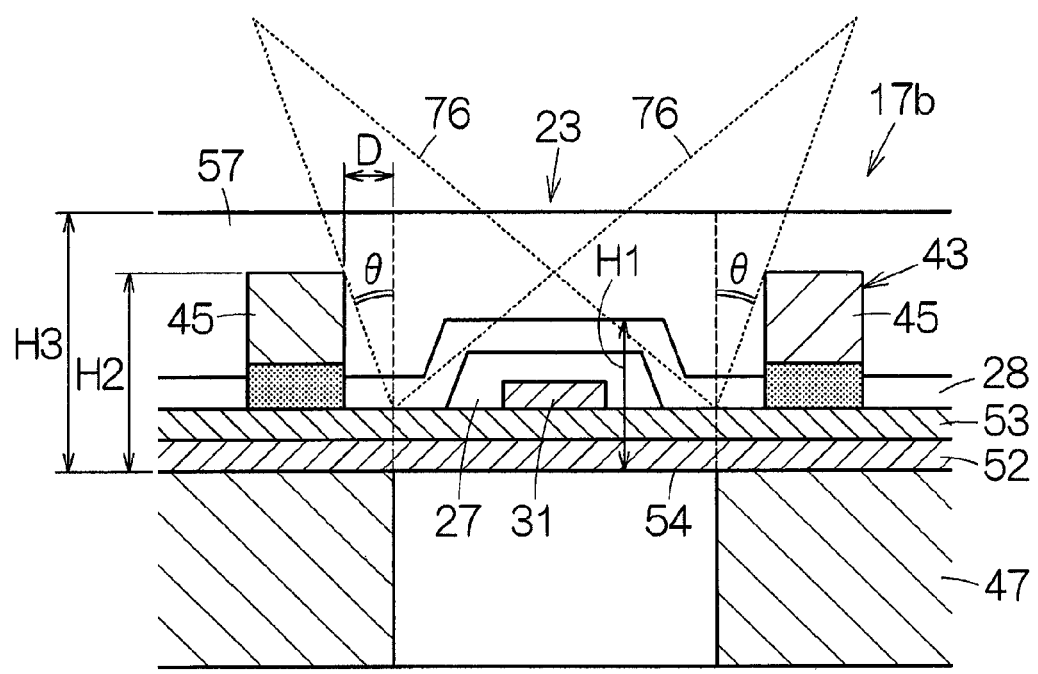
FIG. 13 corresponds to FIG. 5, and the drawing is a partial enlarged cross-section view of an ultrasonic transducer element unit according to the third embodiment.

FIG. 13 schematically shows a configuration of the element unit 17b according to the third embodiment. In the third embodiment, the second long pieces 45 of the grid element 43 have the second height H2 which is lower than the third height H3 of the protection film 57. The second height H2 is higher than the first height H1 of the element 23. Here, the thickness of the protection film 57 maintains in the same manner as the previous description so that the protection film 57 can be functioned as an acoustic matching layer. The grid element 43 can receive the reaction force from the target earlier than the element 23. The grid element 43 supports the reaction force from the target. In addition, the height of the grid element 43 is suppressed so that for preventing interference between the second long pieces 45 and the ultrasonic beam 76, the second long pieces 45 can be close to the vibrating membrane 54 compare to the first and the second embodiments. Therefore, the density of the elements 23 can be improved. Here, the height of the first long pieces 44 can be made to coincide the second long pieces 45 or can be made to coincide the protection film 57. Other configurations are the same as the previous description.

(7) Ultrasonic Transducer Element Unit According to Still Another Embodiment

Figure 14:
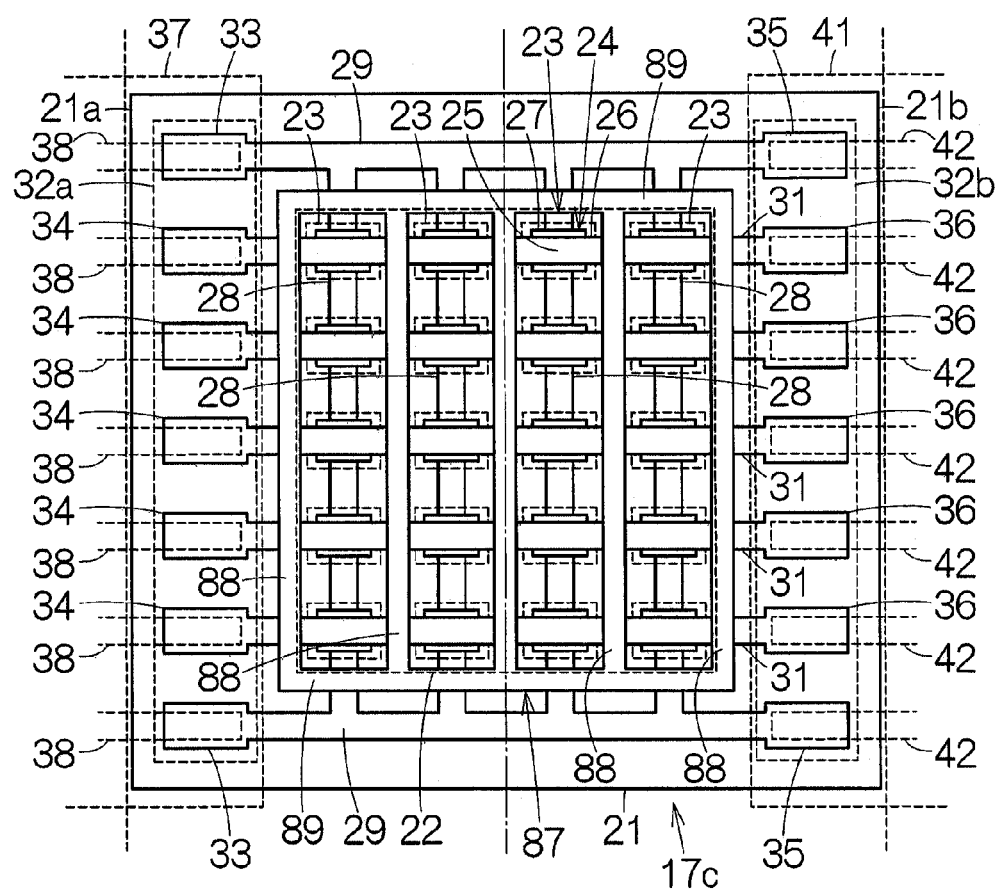
FIG. 14 corresponds to FIG. 3, and the drawing is a partial enlarged plan view of an ultrasonic transducer element unit according to the fourth embodiment.

FIG. 14 schematically shows a configuration of the element unit 17c according to the fourth embodiment. In the fourth embodiment, the grid element 87 instead of the grid element 43 of the previous description is fixed on the surface of the base body 21. This grid element 87 has the first long pieces (wall portions) 88 that are arranged between the columns of the elements 23 and extend in parallel to each other. Here, the first long pieces 88 are arranged relative to the both sides of the columns of the elements 23, respectively. The first long pieces 88 are connected to each other in a pair of the second long pieces 89 extending in a row direction in outside of the outline of the element array 22. A space of one line is constituted between the first long pieces 88 that are adjacent to each other. An obstacle is not existed between the long pieces 88. Other configurations are the same as the previous description.

In the element unit 17c, for example, for realizing a sector scanning, the ultrasonic beam scans around the rotation axis extending in a row direction in each of the elements 23. In the grid element 87, the first long pieces 88 are arranged parallel to a scanning direction of the ultrasonic beam. An obstacle is not existed in a scanning direction of the ultrasonic beam. As a result, the interference between the grid element 87 and the ultrasonic beam can be avoided. The long pieces are not arranged between the elements 23 adjacent to each other in a row direction so that a distance in the rows of the elements 23 can be narrowed. The density of the elements 23 can be improved.

(8) Ultrasonic Transducer Element Unit According to Still Another Embodiment

Figure 15:
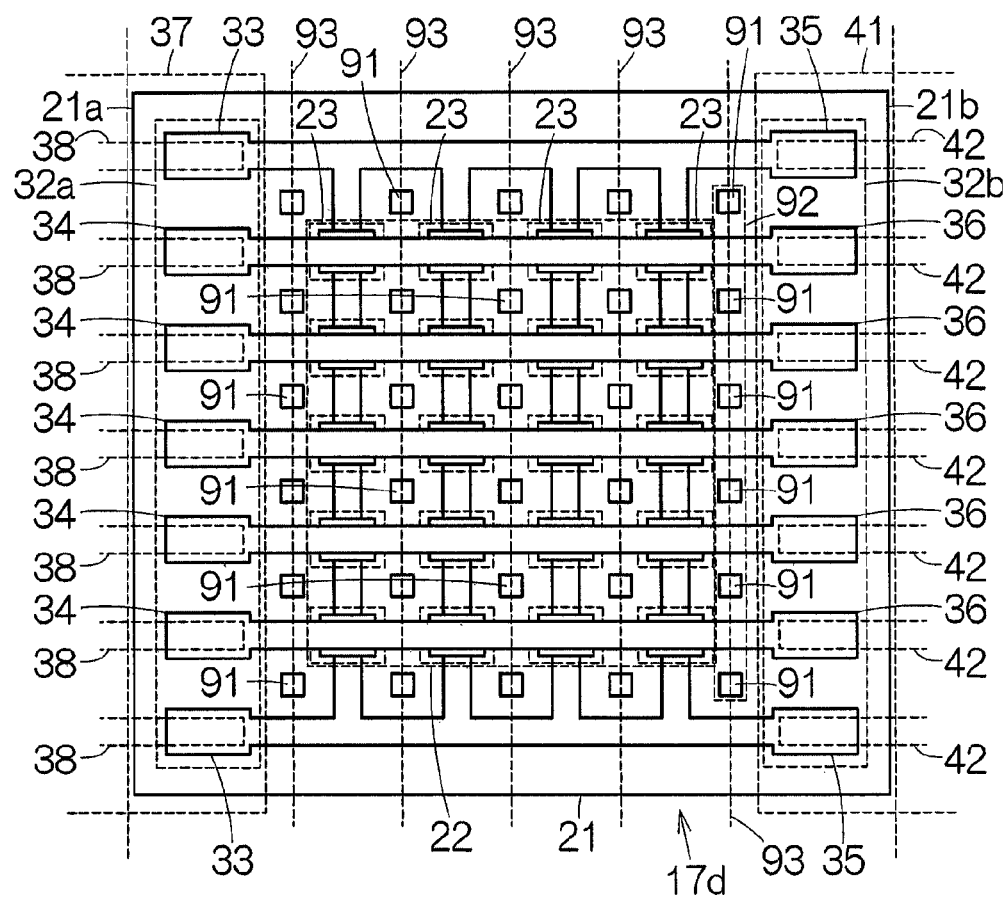
FIG. 15 corresponds to FIG. 3, and the drawing is a partial enlarged plan view of an ultrasonic transducer element unit according to the fifth embodiment.

FIG. 15 schematically shows a configuration of the element unit 17d according to the fifth embodiment. In the fifth embodiment, a collective entity 92 of projections 91 instead of the grid element 43 of the previous description is fixed on the surface of the base body 21. The collective entity 92 of the projections 91 has a plurality of projections 91 arranged in a grid-point pattern. Specifically, in each of the collective entities 92, the projections 91 are lined on virtual parallel lines 93 defined in parallel to a column direction of the element array 22 on the surface of the base body 21, and they are arranged between the columns of the elements 23. Here, the collective entities 93 are arranged relative to the both sides of the columns of the elements 23, respectively. The projections 91 are arranged outside of the outline (corresponding to the outline of the vibrating membrane 54) of each element 23. A space is provided between the collective entities 92 adjacent to each other in a column direction. An obstacle is not existed. Other configurations are the same as the previous description.

In the element unit 17d, for example, for realizing a sector scanning, the ultrasonic beam scans around the rotation axis extending in a row direction in each of the elements 23. Thus, an obstacle is not existed in a scanning direction of the ultrasonic beam. As a result, the interference between the projections 91 and the ultrasonic beam can be avoided. The projections are not arranged between the elements 23 adjacent to each other in a row direction so that a distance in the rows of the elements 23 can be narrowed. The density of the elements 23 can be improved.

While the present embodiment has been explained in detail as above, it will be apparent to those skilled in the art that various modifications can be made herein without substantially departing from the new matters and the effect of the present invention. Therefore, all such modifications are included in the scope of the invention. For example, the terms used in the specification or the drawings at least once together with a different term having a broader or similar meaning can be replaced with the different term in any portion of the specification or the drawings. Also, the configurations and operations of the ultrasonic diagnostic device 11, the ultrasonic probe 13, the probe head 13b, the element units 17, 17a, 17b, 17c, and 17d, the element 23 and the like are not limited to the present embodiment, and various modifications are possible.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the invention are provided for illustration only, and not for the purpose of limiting the invention as defined by the appended claims and their equivalents

What is claimed is:

1. An ultrasonic transducer element unit comprising:
   a substrate including a main surface, an opposite surface that is opposite the main surface in a first direction of a thickness direction of the substrate, and inner surfaces that are arranged between the main surface and the opposite surface and define openings that are arranged in an array pattern and penetrate the substrate from the main surface and the opposite surface in the first direction;
   a flexible film formed on the main surface; and
   an element array forming a plurality of columns and rows with each column and row including a plurality of ultrasonic transducer elements such that the ultrasonic transducer elements are arranged, on the flexible film, in a second direction of the thickness direction relative to the openings, respectively, the second direction being opposite the first direction, the ultrasonic transducer elements including piezoelectric films, respectively, which are arranged such that the piezoelectric films do not overlap the inner surfaces of the substrate in a plan view in the thickness direction, each of the ultrasonic transducer elements having a first height in the thickness direction from the main surface; and
   a grid element arranged in the second direction relative to the main surface, arranged not to overlap the ultrasonic transducer elements in the plan view, and having a second height which is greater than the first height in the thickness direction,
   the grid element being a one-piece single material unitary member fixed on the flexible film with an adhesive layer, the grid element having a plurality of first elongated projecting portions that extend along the columns and a plurality of second elongated projecting portions that extend in the rows in the plan view, wherein the top surface of the grid element is uncovered
   the ultrasonic transducer elements including a first ultrasonic transducer element arranged corresponding to a first opening of the openings and a second ultrasonic transducer element arranged corresponding to a second opening of the openings, the first ultrasonic transducer element and the second ultrasonic transducer element being adjacent each other such that one of the first and second elongated projecting portions is arranged between the first and second ultrasonic transducer elements, the first ultrasonic transducer element having a first piezoelectric film with a first surface facing toward the one of the first and second elongated projecting portions, the second ultrasonic transducer element having a second piezoelectric film with a second surface facing toward the one of the first and second elongated projecting portions,
   a distance between the first surface of the first piezoelectric film and the one of the first and second elongated projecting portions being equal to a distance between the second surface of the second piezoelectric film and the one of the first and second elongated projecting portions in the plan view.

2. The ultrasonic transducer element unit according to claim 1, further comprising
   a protection film configured to cover the first ultrasonic transducer element and having a surface at the second height.

3. The ultrasonic transducer element unit according to claim 1, wherein
   as a distance increases from the main surface, a first side surface of the one of the first and second elongated projecting portions, which faces the first ultrasonic transducer element is inclined in a direction away from the first ultrasonic transducer element.

4. A probe including the ultrasonic transducer element unit according to claim 1, the probe comprising:
   a case supporting the first ultrasonic transducer element unit.

5. An electronic device including the probe according to claim 4, the electronic device comprising:
   a processing circuit being connected to the probe and being configured to control the first ultrasonic transducer element to output.

6. An ultrasonic diagnostic device including the probe according to claim 4, the ultrasonic diagnostic device comprising:
   a processing circuit being connected to the probe, controls the first ultrasonic transducer element to output, and generates an image, and
   a display device being configured to display the image.

7. A probe head including the ultrasonic transducer element unit according to claim 1, the probe head comprising:
a case supporting the ultrasonic transducer element unit.

8. The ultrasonic transducer element unit according to claim 3, wherein
the one of the first and second elongated projecting portions further includes a second side surface that is arranged apart from the first side surface and faces the second ultrasonic transducer element, and
as a distance increases from the main surface, the second side surface is inclined in a direction close to the first ultrasonic transducer element.

9. The ultrasonic transducer element unit according to claim 1, wherein
the first ultrasonic transducer element is configured to irradiate ultrasonic beam, the one of first and second elongated projecting portions has a first side surface facing the first ultrasonic transducer element, and
the first side surface is arranged, in the plan view, apart from the first opening by a distance that is determined according to a maximum angle of the ultrasonic beam, and the maximum angle is defined between a linear path of the ultrasonic beam and an imaginary line that extends along the second direction from one of the inner surfaces, which is the closest to the first side surface.

10. An ultrasonic transducer element unit comprising:
a substrate including a main surface, an opposite surface that is opposite the main surface in a first direction of a thickness direction of the substrate, and inner surfaces that are arranged between the main surface and the opposite surface and define openings arranged in columns and rows in an array pattern;
an element array including a first ultrasonic transducer element arranged in a second direction of the thickness direction relative to a first opening of the openings and a second ultrasonic transducer element arranged in the second direction relative to a second opening of the openings, the second direction being opposite the first direction,
the first ultrasonic transducer element having a first piezoelectric film that does not overlap the inner surfaces of the substrate in a plan view in the thickness direction, the second ultrasonic transducer element having a second piezoelectric film that does not overlap the inner surfaces of the substrate in the plan view; and
a grid element arranged not to overlap with the openings in the plan view on the main surface and having a second height which is greater than the first height in the thickness direction, the grid element being a one-piece single material unitary member fixed on the flexible film with an adhesive layer, the grid element having a plurality of first elongated projecting portions that extend along the columns between the columns and a plurality of second elongated projecting portions that extend along the rows between the rows in the plan view, wherein the top surface of the grid element is uncovered
the first ultrasonic transducer element and the second ultrasonic transducer element being adjacent each other such that one of the first and second elongated projecting portions is arranged between the first and second ultrasonic transducer elements, the first piezoelectric film having a first surface that faces toward the one of the first and second elongated projecting portions, the second piezoelectric film having a second surface that faces toward the one of the first and second elongated projecting portions,
a distance between the first surface of the first piezoelectric film and the one of the first and second elongated projecting portions being equal to a distance between the second surface of the second piezoelectric film and the one of the first and second elongated projecting portions in the plan view.

* * * * *